(12) United States Patent
Janbakhsh (10) Patent No.: US 8,139,713 B2
(45) Date of Patent: Mar. 20, 2012

(54) COMBINED NUCLEAR-RADIOGRAPHIC SUBJECT IMAGING

(75) Inventor: Mahmoud Janbakhsh, San Ramon, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 197 days.

(21) Appl. No.: 12/672,421

(22) PCT Filed: Aug. 6, 2008

(86) PCT No.: PCT/IB2008/053166
§ 371 (c)(1),
(2), (4) Date: Feb. 5, 2010

(87) PCT Pub. No.: WO2009/022271
PCT Pub. Date: Feb. 19, 2009

(65) Prior Publication Data
US 2011/0129061 A1    Jun. 2, 2011

Related U.S. Application Data

(60) Provisional application No. 60/955,079, filed on Aug. 10, 2007.

(51) Int. Cl.
G01N 23/04 (2006.01)
(52) U.S. Cl. .......................... 378/63; 378/19
(58) Field of Classification Search .......................... None
See application file for complete search history.

(56) References Cited

U.S. PATENT DOCUMENTS

| | | | |
|---|---|---|---|
| 6,302,579 B1 | 10/2001 | Meyer et al. | |
| 6,399,951 B1 | 6/2002 | Paulus et al. | |
| 6,448,559 B1 | 9/2002 | Saoudi et al. | |
| 6,490,476 B1 | 12/2002 | Townsend et al. | |
| 2005/0023471 A1 | 2/2005 | Wang et al. | |
| 2005/0152492 A1 | 7/2005 | Yakubovsky et al. | |
| 2005/0157839 A1 | 7/2005 | Altman | |
| 2005/0207526 A1 | 9/2005 | Altman | |
| 2005/0213705 A1 | 9/2005 | Hoffman | |
| 2006/0050839 A1* | 3/2006 | Balan et al. | 378/4 |
| 2008/0081985 A1* | 4/2008 | Zheng et al. | 600/407 |

FOREIGN PATENT DOCUMENTS

| | | | |
|---|---|---|---|
| DE | 19853463 A1 | 5/2000 | |
| WO | 0075691 A1 | 12/2000 | |

* cited by examiner

*Primary Examiner* — Hoon Song (57) ABSTRACT

When performing a patient scan to collect patient data for reconstruction into one or more image volumes, a combination nuclear-radiographic subject imaging device (10) includes first and second detector heads (22a, 22b), which move on respective positionable tracks (14a, 14b). The positionable tracks move on stationary tracks (12) coupled to a rotatable gantry structure (16). Each detector head is rotatably coupled to its positionable track by a rotation arm (24). When a radiographic scan is performed, the first detector head (22a) is rotated so that a radiographic detector (26) mounted to the first detector head (22a) faces the patient, and an X-ray source (28) mounted to the second detector head (22b) also faces the patient, opposite the radiographic detector (26). When a nuclear imaging scan is performed, the detector heads (22a, 22b) are rotated to face the patient during the scan.

27 Claims, 5 Drawing Sheets

COMBINED NUCLEAR-RADIOGRAPHIC SUBJECT IMAGING

CROSS REFERENCE TO RELATED APPLICATIONS

This application claims the benefit of U.S. provisional application Ser. No. 60/955,079 filed Aug. 10, 2007, which is incorporated herein by reference.

DESCRIPTION

The present application finds particular application in computed tomography (CT), single photon emission computed tomography (SPECT), positron emission tomography (PET), and other radiographic and nuclear imaging devices or techniques. However, it will be appreciated that the described technique(s) may also find application in other types of imaging systems and/or other patient scanning systems or techniques.

One conventional SPECT-CT system includes a plurality of SPECT heads, e.g., two heads, mounted to a rotatable gantry. The heads typically have three degrees of motion: along each of two axes that are orthogonal to the axis of rotation of the gantry and are rotatable about a central axis of the SPECT head parallel to the axis of gantry rotation. This enables the SPECT heads to be positioned a minimal distance from the patient and to change radial position and angular orientation as the gantry rotates about the patient.

In the previous generation of SPECT-CT cameras, developed by various manufacturers, the X-ray source and the detector are fixed to a rotatable gantry. The X-ray components are typically static and only move on a circular path around the object, as part of a gantry structure. Retractable or static arms attach the X-ray source and detector to the gantry. Therefore, they have a fixed geometry with respect to the patient being imaged. This, in turn, drives the source power requirements and the detector size, such that traditional SPECT-CT cameras required substantial amounts of power and are undesirably bulky.

In another combined SPECT-CT system, an x-ray source and detector are mounted for movement relative to the two axes of a rotatable rectangular gantry that is perpendicular to the axis of gantry rotation, in order to position the x-ray source and detector on opposite sides of the patient during a CT scan. During the CT scan, the SPECT heads are typically moved to an extreme end of one of the sides of the gantry to move them out of the way of the x-ray source and CT detector. Analogously, during a SPECT scan, the x-ray source and the CT detector are moved to extreme ends of one of the gantry sides so as not to interfere with the SPECT heads during a SPECT scan. Having two (or more) SPECT heads, a CT detector, and an X-ray source all mounted for independent movement on the gantry increases cost and complexity. Additionally, systems that attach the X-Ray source and detector to a SPECT machine have often a fixed distance between the source, object, and detector, and thus are constrained to function as one-size-fits-all systems and suffer from imaging point-of-view limitations. That is, such systems require a common power level for all different patient sizes.

Thus, there is an unmet need in the art for systems and methods that facilitate overcoming the deficiencies described above.

In accordance with one aspect, a system for combination nuclear-radiographic subject imaging device includes a first nuclear detector head having a nuclear radiation receiving face that is rotatably mounted on a gantry, and a second nuclear detector head that is mounted on the gantry across an examination region opposite the first head. The system further includes a radiographic detector that is coupled to a back surface of the first detector head, and an X-ray source that is positionable to direct a generated X-ray beam across the examination region to the radiographic detector. The first head is rotated to position the radiographic detector opposite the X-ray source and facing a volume of interest when a radiographic scan is performed and is rotated to position its nuclear radiation receiving face facing the volume of interest when a nuclear scan is performed.

In accordance with another aspect, a method of method of performing sequential radiographic and nuclear imaging scans includes positioning a radiographic detector head and an X-ray source about a volume of interest and performing the radiographic scan, rotating a first detector head approximately 180° and positioning a nuclear radiation receiving face to face the volume of interest, and positioning a second detector head to face the volume of interest. The method further includes performing the nuclear scan of the volume of interest.

Yet another aspect relates to a patient imaging system, including a processor or means for performing a nuclear imaging scan on a patient, and a processor or means for performing a radiographic scan on the patient. The system further includes a processor or means for rotating first and second detector heads on a arm to face away from the patient when the radiographic scan is performed, such that a radiographic detector head mounted to the first detector head faces the patient, and an X-ray source mounted to the second detector head faces the patient, during the radiographic scan. The system additionally includes a processor or means for moving the first and second detector heads with attached radiographic detector head and X-ray source along respective movable tracks to a desired position relative to the patient, and for moving the movable tracks along stationary tracks to a desired position relative to the patient.

Yet another aspect relates to a method for in-line imaging of anatomic data with functional imaging, including, performing an anatomic imaging scan and a functional imaging scan of a subject, wherein functional imaging heads are not in-line during the anatomic imaging scan, and wherein anatomic imaging heads coupled to the functional imaging heads are not in-line during the functional imaging scan.

One advantage is that resides in reduced complexity and weight.

Another advantage is that system size and detector head number are reduced.

Another advantage resides in fewer servos are used to move detector heads into and out of position.

Another advantage resides in improved setup time and patient throughput.

Another advantage resides in improved registration of images.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
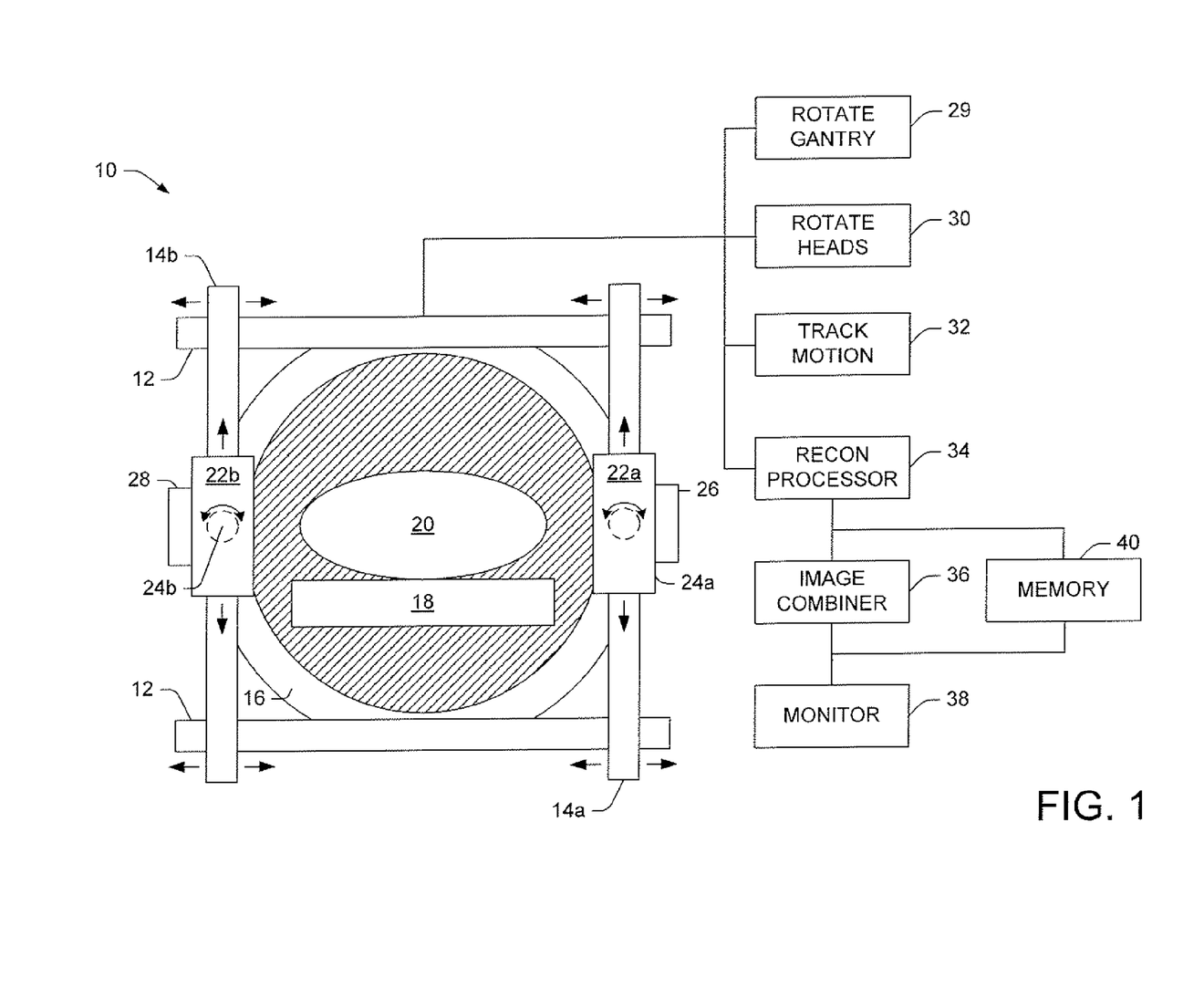
FIG. 1 illustrates a combined SPECT-CT scanner that facilitates streamlining size and functionality for a subject imaging device (SID).

FIG. 1 illustrates a combined SPECT-CT scanner that facilitates streamlining size and functionality for a subject imaging device (SID) 10. The SID can include a gantry structure with a pair of stationary beams or tracks 12, along which positionable beams or tracks 14a, 14b move to position imaging devices horizontally (in the rotational direction of FIG. 1) about a rotatable gantry 16. In other embodiments, the tracks have different geometries, and need not be linear. For example, a one or more of the tracks 12, 14a, 14b can be curved, angled, etc., to facilitate reducing overall system size and/or cost.

A support 18 provides a surface on which a volume of interest 20 (e.g., a subject, a patient, or the like) rests. Each positionable track 14a, 14b has a nuclear camera head (NCH) 22a, 22b positioned thereon, which moves along the track. In this manner, the NCH can be placed at any desired location or coordinate about the volume of interest. Additionally, each NCH is mounted to the positionable track on a rotating arm or shaft 24a, 24b that permits the NCH to be rotated about an axis parallel to a rotational axis of the gantry. The rotational positioning of the NCH facilitates following a subject's contour.

The SID 10 additionally includes a gantry rotation control module 29 rotating the gantry about a longitudinal axis there through, and a head rotation module 30 for controlling the rotation of the NCH(s) and associated components. For instance, the rotation module 30 can include one or more servo motors or other electrical and/or mechanical means for effectuating rotation of the NCH. The SID further includes a module 32 for controlling track motion, which governs movement of the tracks 14 along the tracks 12 and/or movement of the NCH up and down its track 14. A reconstruction processor 34 is coupled to the SID and reconstructs SPECT, CT or X-ray, or other image information captured by the SID. Reconstructed image data is received by an image combiner 36, which combines the image data for presentation to a user via a monitor 38 or other graphical user interface. Image data generated by the SID (e.g., SPECT data, CT data, PET data, etc.), as well as reconstructed image data, combined image data, etc., is stored to memory 40. In one embodiment, patient translation between and/or during respective scans is mitigated, which facilitates reducing and/or eliminating detrimental effects associated with patient motion and the like.

In one embodiment, the NCH is a SPECT imaging device, and a CT detector 26 is mounted on the rear surface of a SPECT detector 22. In preparation for SPECT imaging, a SPECT detector 22a is rotated under the control of the head rotation module 30 about the rotating arm to face the patient or volume of interest 20. In preparation for CT imaging, the CT detector 26 is rotated to face the patient. This mitigates a need for an entire separate detector head and associated drive mechanism for positioning it. In another embodiment, an X-ray tube or other radiation source 28 is mounted on the back surface of the other SPECT head 22b. This mitigates a need for another head and mechanisms to move it. The design takes advantage of existing motion for the SPECT detector heads 22, and thus overcomes problems associated with conventional methods of attaching an X-ray source and detector to a SPECT machine.

The attachment of CT detector to the back of the SPECT detector mitigates problems associated with mounting multiple detectors and sources to a gantry structure, by taking advantage of the existing radial movement. This in turn allows the CT, or X-ray, source and detector to get as close as desired to the object, thus reducing the X-ray dosage based on patient or subject size, and thereby reducing power requirements and improving image resolution. In another embodiment, a variable gantry aperture is used, based on the patient or subject size, to maximize the efficiency of the system. In one embodiment, an X-ray detector is employed in place of or in addition to the CT detector for planar imaging and the like.

In another embodiment, the NCH is a PET detector head. For instance, a plurality of PET detector heads (e.g., 4) can be mounted on rotating arms 24 on the positionable tracks, and can be positioned and/or pivoted into a desired array about the volume of interest. The CT detector can be mounted to the rear surface of one of the PET detector heads on a first positionable track, and the X-ray source can be mounted to another of the PET detector heads on the opposite positionable track.

In yet another embodiment, the CT detector and/or X-ray source are hinged at the top, bottom, or side of the NCH(s) and are folded outward from the NCH(s) when needed to perform a CT scan. For instance, the CT detector (or X-ray component) can be folded outward approximately 180° from the back of the SPECT detector to which it is mounted, to face the patient for a CT scan. In another example, the CT detector and/or X-ray source is folded outward approximately 90° from the back of the SPECT detector to which it is mounted, and the unit can be rotated approximately another 90° to position the CT detector and X-ray source to face the patient. When not in use, the CT detector and/or X-ray source are stowed in a folded position at against the back of the NCH(s). This configuration can be employed in place of or in addition to the rotating arm 24. In another embodiment, the CT detector and/or X-ray source are hinged to and lie flat against a top or bottom surface of the SPECT detector, and are folded outward approximately 90° to face the patient when a CT scan is to be performed. In another embodiment, the CT detector and/or X-ray source are fixed to the top or bottom surface of their respective SPECT detectors, and rotated approximately 90° to face the patient by the rotating arm 24.

In a further embodiment, functional imaging heads (e.g., SPECT, PET, etc.) have anatomic imaging heads (e.g., CT or X-ray source and detector) coupled thereto, and are rotated or otherwise positioned to bring the respective detector heads in-line (e.g., facing a subject) during a given scan. In this embodiment, functional detector heads are not in-line during the anatomic imaging scan, and anatomic imaging heads are not in-line during the functional imaging scan. Image data generating during the different scans is inherently registered and a reconstruction processor generates a combined functional-anatomic image of the subject.

Figure 2:
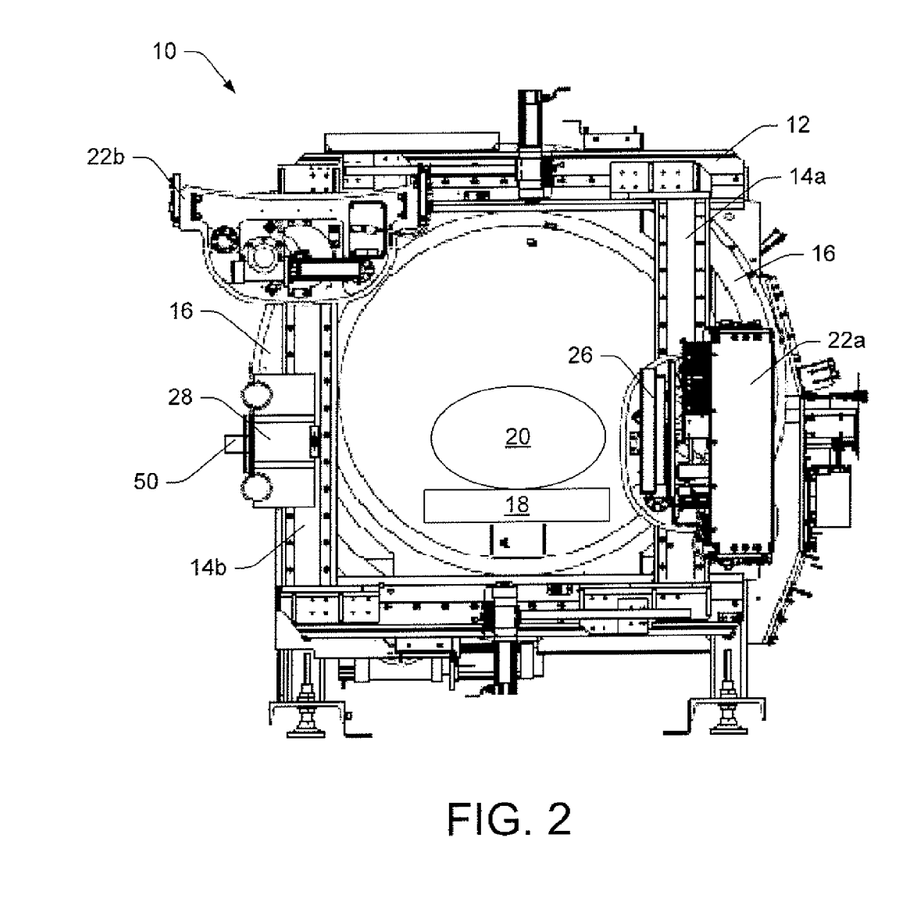
FIG. 2 illustrates a combined SPECT-CT system with an X-ray source mounted to a beam that moves in a circular path about the subject, while the CT detector that receives emitted X-rays is mounted to a rear surface of the SPECT detector head.

FIG. 2 illustrates a combined SPECT-CT system with an X-ray source 28 mounted by a post 50. The CT detector head 26 that receives emitted X-rays is mounted to a rear surface of the SPECT detector head 22a. The attachment of the CT detector head 26 to the SPECT detector 22a, and the X-ray source 28 to the movable track 14b facilitates positioning the X-ray source and detector about the subject in any desired orientation. This configuration eliminates the need for providing a complicated mechanism to retract the X-ray source and detector from the path of the all the SPECT component motion. Additionally, the mobility of the SPECT detector heads (e.g., radially and circumferentially) is imported to the CT detector and source, which permits positioning thereof very close to a patient. This facilitates isolating a target region in the patient, which in turn permits a lower X-ray dosage to be administered, thus protecting the patient without compromising image data quality or quantity.

As illustrated, the SID includes stationary tracks 12 upon which moveable tracks 14 slide to move closer and further apart. CT detector head 26 is positioned near a volume of interest 20, while SPECT detector head 22*b* is stowed out of the way at an extreme end of its positionable track. The X-ray source 28 is positioned opposite the CT detector head 26, on the post 50 that is mounted to the gantry 16 and moves in a circumferential path about the volume of interest 20. In one embodiment, the X-ray source 28 is mounted to the gantry 16 midway between the stationary tracks to center the X-ray beam on the axis of gantry rotation. The X-ray source rotates about the post to move further from the gantry axis of rotation to provide greater clearance for the SPECT head 22*b* during SPECT imaging. In another embodiment, the post 50 is slidably mounted on the movable track 14*b*, which in turn is mounted to the gantry 16. During SPECT imaging, the X-ray source is moved to one end of the movable track 14*b*. The CT detector 26 is mounted to the back of the SPECT detector head 22*a*, and is rotated into position (e.g., the combination SPECT detector head 22*a* and CT detector 26 is rotated 180°) to face the X-ray source 28 for CT or other radiographic imaging.

According to an example, a patient 20 is positioned in the gantry 16 on the support 18 for one of both of a SPECT imaging scan and a CT scan. An operator enters one or more commands that move the SPECT detector 22*b* to a stowed position, rotate the combination SPECT detector 22*a* and CT detector 26 into position for a CT scan (e.g., such that the CT detector head 26 is facing the patient), and position the X-ray source 28 opposite the CT detector head 26. The gantry 16 rotates the X-ray source 28 and the CT detector 26 around the patient, typically keeping the X-ray source-to-detector spacing constant. The CT data is sent to the reconstruction processor 34 for reconstruction. The CT data can be used to generate a CT image for display, to generate corrections for the SPECT scan, or the like. The SPECT detectors 22 are positioned on either side of the patient. The movable tracks move inward and outward as the gantry rotates to maintain the SPECT head adjacent the patient as SPECT image data is collected. SPECT data is transmitted to a reconstruction processor, such as described above. The SPECT and CT images can be combined in various ways or can be displayed separately. Alternatively, the SPECT scan can be performed first, and the detector heads X-ray source can be repositioned for a subsequent CT scan, if desired. In one embodiment, the rotation module 30 and track motion module 32 ensure that respective components are in position at appropriate times, so that the X-ray source 28 is not positioned opposite the face of the SPECT detector 22*a* and/or the SPECT detector 22*b* is not positioned opposite the CT detector 26 at the time of scanning.

Figure 3:
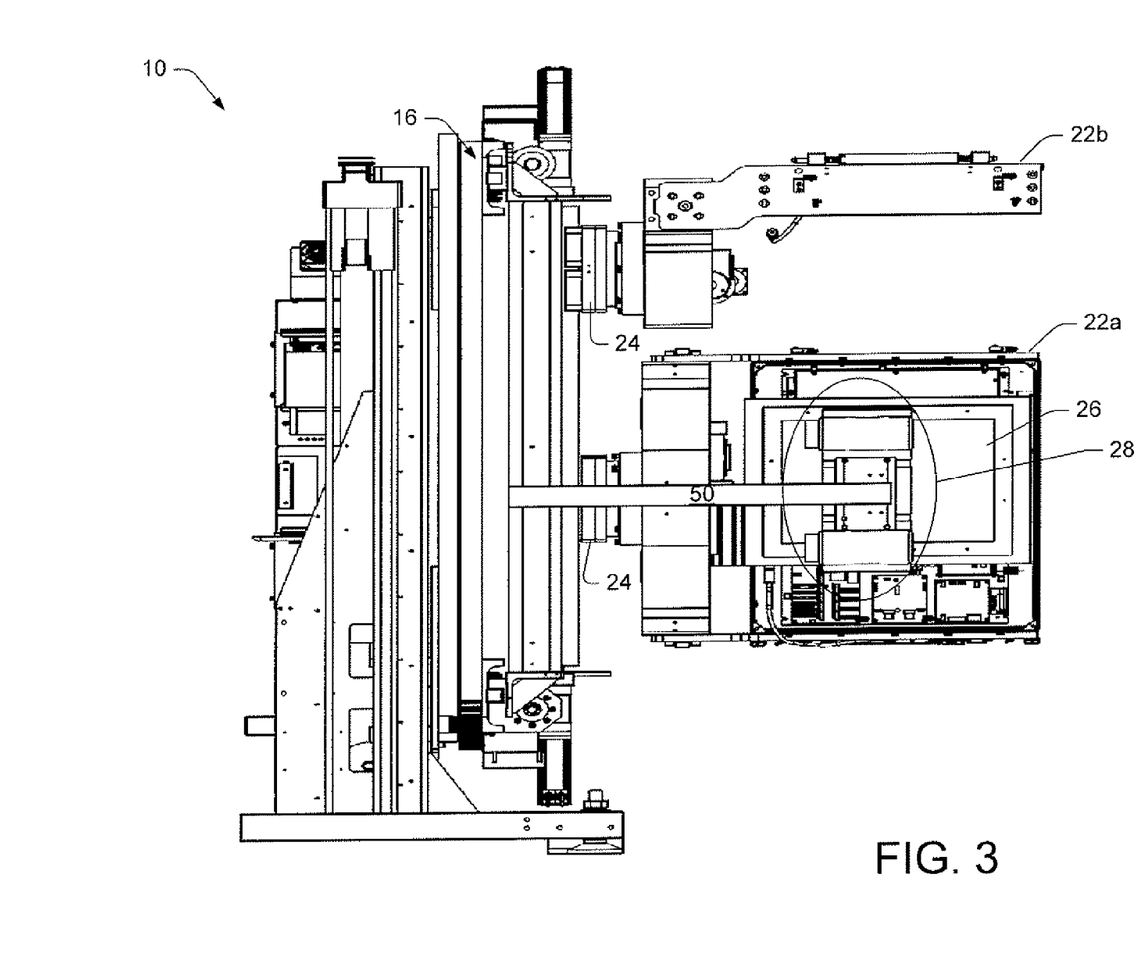
FIG. 3 illustrates a side view of the SID with the X-ray source attached to the gantry by a shaft.

FIG. 3 illustrates a side view of the SID 10 with the X-ray source 28 attached to the gantry by the post 50. As described above, in an alternative embodiment the X-ray source is mounted to the rear-face of the SPECT detector head 22*b*, as described in FIG. 1. Each SPECT detector head 22*a*, 22*b*, is mounted to its respective movable track by a rotating arm 24, which rotates the SPECT detector head into a desired orientation, and which slides along the movable track 14*a*, 14*b* to position the detector head. The SPECT detector head 22*a* with CT detector, mounted to its back surface is positioned by movement along the movable tracks 14*a*, 14*b*, movement of the movable track 14*a* along the stationary tracks 12, and/or rotational movement about the axis through the rotating arm (s) 24. The X-ray source can be positioned by movement of the post 50 about the circumference of the gantry 16.

In other embodiments, different combinations of PET, SPECT, CT, and/or X-ray components are coupled together and rotated into position for a desired scan. For instance, in one embodiment, PET detectors are mounted to SPECT detectors, and are rotated or unfolded into position for a PET scan. In another embodiment, PET and CT detectors (e.g., and an X-ray source for the CT scans) are co-mounted. In still another embodiment, a three-sided NCH includes a SPECT detector, a CT detector and a PET detector, and a plurality of such NCHs are positioned about a patient or volume of interest, with respective detectors positioned to face the patient for respective scans. Moreover, a single detector surface can be used for both PET and SPECT scans, if desired.

In another embodiment, collision avoidance is provided, whereby NCHs are not permitted to rotate during a scan (e.g., SPECT, PET, CT, X-ray, etc.) to ensure that only desired detector faces are oriented toward the patient during a desired scan. For instance, during a given scan, the rotating arms 24 can be locked (e.g., mechanically, electronically, electrically, etc.) to facilitate keeping the appropriate surfaces facing the patient. Additionally or alternatively, in an embodiment where one or more devices is hinged to an NCH, the hinge mechanisms can be locked as well.

Figure 4:
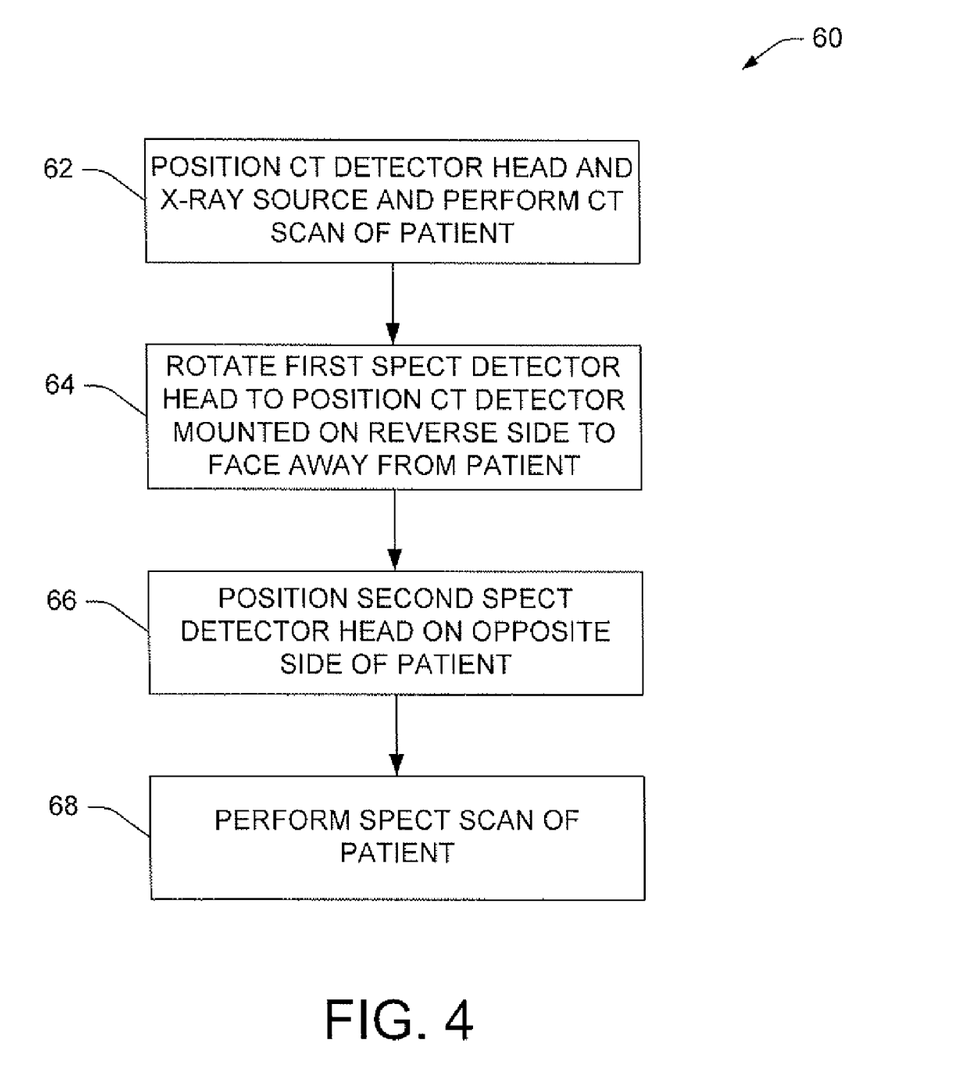
FIG. 4 illustrates a method for performing the dual SPECT-CT scan of a patient using the rotatable combination detector heads.

FIG. 4 illustrates a method 60 for performing the dual SPECT-CT scan of a patient using the combination detector heads described above. At 62, the X-ray source and CT detector head are positioned to face a patient or other volume of interest, and a CT scan is performed to generate image data. Positioning of the various detector heads and/or the X-ray source can be performed by movement and/or rotation on the tracks. The X-ray source is mounted to a post attached to the gantry or mounted to the back of the second SPECT detector head and rotated into position facing the patient. At 64, a first SPECT detector head is rotated toward from the patient, and the CT detector mounted to the back of the first SPECT detector head is thus rotated away from the patient. At 66, the second SPECT detector head is positioned opposite the first SPECT detector head, on the other side of the patient. At 68, a SPECT scan of the patient is performed to generate SPECT image data. It will be appreciated that the CT scan may be performed after to the SPECT scan, if desired. Additionally or alternatively, the CT detector and/or X-ray source can be mounted to a back surface of different PET detectors, and a combined PET-CT scan can be performed in the manner described above.

In SPECT imaging, a projection image representation is defined by the radiation data received at each coordinate on the detector head. In SPECT imaging, a collimator defines the rays along which radiation is received. As stated above, it will be appreciated that although various embodiments are described with regard to SPECT images, positron emission tomography (PET) imaging systems can additionally or alternatively be employed to perform the techniques presented herein.

In PET imaging, the detector head outputs are monitored for coincident radiation events on two heads. From the position and orientation of the heads and the location on the faces at which the coincident radiation is received, a ray between the coincident event detection points is calculated. This ray defines a line along which the radiation event occurred. In both PET and SPECT, the radiation data from a multiplicity of angular orientations of the heads is stored to data memory, and then reconstructed by a reconstruction processor into a transverse volumetric image representation of the region of interest, which is stored in a volume image memory.

Figure 5:
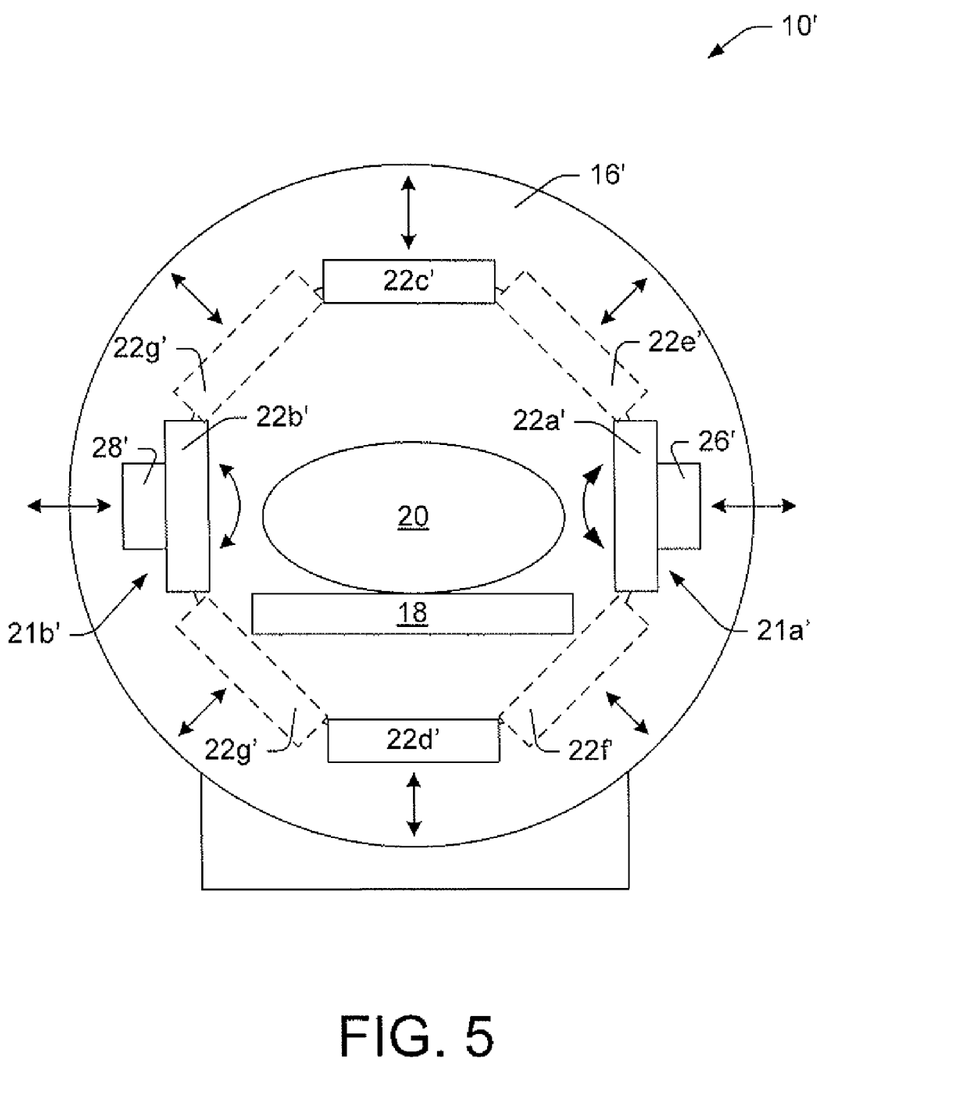
FIG. 5 illustrates another embodiment of a combined SPECT-CT scanner.

In FIG. 5, a head 21a' with a CT detector 26' on one side and a SPECT or PET detector 22a' on the other side is rotatably mounted to a rotatable ring gantry 16' for radial movement in and out. A head 21b' with an X-ray source 28' and a SPECT or PET detector 22b' on the other side is mounted to the rotating gantry opposite the head 21a' for radial movement in and out. Additional SPECT or PET heads 22c' and 22d' are mounted to the rotating gantry 16'.

In one PET-CT embodiment, a number of PET-only heads (22c' and 22d', and optionally 22e', 22f', 22g', and 22h') are stationary-mounted to the ring gantry 16', and abut each other to form a ring of PET detectors with PET detectors 22a' and 22b' rotated so that their PET detectors face inward. For CT or other radiographic imaging, the heads 21a' and 21b' are rotated such that their X-ray source and CT detector face each other.

The invention claimed is:

1. A combination nuclear-radiographic subject imaging device, including:
   a first nuclear detector head having a nuclear radiation receiving face that is rotatably mounted on a gantry;
   a second nuclear detector head that is mounted on the gantry across an examination region opposite the first head;
   a radiographic detector that is coupled to a back surface of the first detector head; and
   an X-ray source that is positionable to direct a generated X-ray beam across the examination region to the radiographic detector;
   wherein the first head is rotated to position the radiographic detector opposite the X-ray source and facing a volume of interest when a radiographic scan is performed and is rotated to position its nuclear radiation receiving face facing the volume of interest when a nuclear scan is performed.

2. The system according to claim 1, wherein the first and second detector heads are each rotatably coupled to first and second movable tracks by a arms, the arms being mounted for movement along respective movable tracks to position the first and second detector heads.

3. The system according to claim 2, wherein the movable tracks are movably coupled to stationary tracks, which are fixedly mounted to the gantry, the movable tracks being movable toward and away from each other along the stationary tracks.

4. The system according to claim 3, wherein the X-ray source is coupled to a movable post that moves the X-ray source along the second movable track.

5. The system according to claim 1, wherein the X-ray source is coupled to a back surface of the second detector head, which is rotated to position the X-ray source facing the volume of interest when a radiographic scan is performed.

6. The system according to claim 1, further including:
   a reconstruction processor that receives nuclear data from the first and second detector heads and the radiographic detector, and reconstructs the nuclear data into a SPECT or PET image and the radiographic data into a CT image.

7. The system according to claim 5, further including:
   an image combiner that combines the SPECT or PET image volume and the CT image volume into a combined SPECT-CT or PET-CT image; and
   a monitor on which the combined SPECT-CT or PET-CT image is displayed to a user.

8. The system according to claim 7, wherein the radiographic detector or the X-ray source pivots about its respective nuclear head.

9. The system according to claim 1, further including a processor programmed to execute non-transitory computer-executable instructions including:
   a routine for positioning the radiographic detector head and the X-ray source about the volume of interest and performing the radiographic scan;
   a routine for rotating the first detector head approximately 180° and positioning the nuclear radiation receiving face to face the volume of interest;
   a routine for positioning the second detector head to face the volume of interest; and
   a routine for performing the nuclear scan of the volume of interest.

10. A method for performing the combined nuclear-radiographic scan in the system of claim 1, including:
    positioning the radiographic detector head and the X-ray source about the volume of interest and performing the radiographic scan;
    rotating the first detector head approximately 180° and positioning the nuclear radiation receiving face to face the volume of interest;
    positioning the second detector head to face the volume of interest; and
    performing the nuclear scan of the volume of interest.

11. A method of performing sequential radiographic and nuclear imaging scans, including:
    positioning a radiographic detector head and an X-ray source about a volume of interest and performing the radiographic scan;
    rotating a first detector head and positioning a nuclear radiation receiving face to face the volume of interest;
    positioning a second detector head to face the volume of interest; and
    performing the nuclear scan of the volume of interest;
    wherein the radiographic detector head is mounted to one of a back surface of the first detector head, a top surface of the first detector head, and a bottom surface of the first detector head.

12. The method according to claim 11, wherein positioning the radiographic detector head includes rotating the first detector head approximately 180° when the radiographic detector head is mounted to the back surface of the first detector head.

13. The method according to claim 11, wherein positioning the radiographic detector head includes rotating the first detector head approximately 90° when the radiographic detector head is mounted to the top or bottom surface of the first detector head.

14. The method according to claim 11, wherein positioning the X-ray source includes moving the X-ray source circumferentially around a circular gantry to which the X-ray source is attached by a movable rod.

15. The method according to claim 11, wherein the X-ray source is mounted to a back surface of the second detector head.

16. The method according to claim 15, wherein positioning the X-ray source includes rotating the second detector head approximately 180°.

17. The method according to claim 11, wherein the X-ray source is mounted to a top or bottom surface of the second detector head.

18. The method according to claim 17, wherein positioning the X-ray source includes rotating second detector head approximately 90°.

19. The method according to claim 11, wherein the radiographic detector head is mounted to the back surface of the first detector head, the X-ray source is mounted to a back surface of the second detector head, and positioning the radiographic detector head and the X-ray source includes rotating the first and second detector heads approximately 180°.

20. A processor or non-transitory computer-readable medium programmed to execute computer executable instructions for performing the method of claim 11.

21. The method according to claim 11, wherein the radiographic detector head is mounted to a surface of the first detector head, and wherein positioning the radiographic detector head includes folding the radiographic detector head outward to face the volume of interest.

22. The method according to claim 11, further including interleaving a SPECT or PET image of the patient, generated from the nuclear scan, and a CT image of the patient generated from the radiographic scan, without patient translation between and during the nuclear and radiographic scans.

23. The method according to claim 11, further including locking the first and second detector heads, the radiographic detector head, and the X-ray source into their respective positions during at least one of the nuclear scan or the radiographic scan.

24. A patient imaging system, including:
   a processor or means for performing a nuclear imaging scan on a patient;
   a processor or means for performing a radiographic scan on the patient;
   a processor or means for rotating first and second detector heads on an arm to face away from the patient when the radiographic scan is performed, such that a radiographic detector head mounted to the first detector head faces the patient, and an X-ray source mounted to the second detector head faces the patient, during the radiographic scan; and
   a processor or means for moving the first and second detector heads with attached radiographic detector head and X-ray source along respective movable tracks to a desired position relative to the patient, and for moving the movable tracks along stationary tracks to a desired position relative to the patient.

25. A method for in-line imaging of anatomic data with functional imaging, including:
   performing an anatomic imaging scan and a functional imaging scan of a subject;
   wherein functional imaging heads are not in-line during the anatomic imaging scan;
   wherein anatomic imaging heads coupled to the functional imaging heads are not in-line during the functional imaging scan;
   wherein the anatomic imaging heads are respectively mounted to one of a back surface of the functional detector heads, a top surface of the functional detector head, and a bottom surface of the functional detector heads; and
   wherein the functional imaging heads a rotated to an in-line orientation when performing the functional imaging scan, and the anatomic imaging heads a rotated to an in-line orientation when performing the anatomic imaging scan.

26. The method according to claim 25, further including rotating the functional imaging heads to bring the anatomic imaging heads in-line during the anatomical imaging scan, and rotating the functional imaging heads to bring them in-line during the functional imaging scan.

27. The method according to claim 25, wherein anatomic and functional data generated during the respective scans are inherently registered to generate a combined anatomic and functional image of the patient.

* * * * *